(12) United States Patent
Wagner et al.

(10) Patent No.: US 6,667,310 B2
(45) Date of Patent: Dec. 23, 2003

(54) SUBSTITUTED GUANIDINE DERIVATIVES

(75) Inventors: Klaus Wagner, Neubeuern (DE); Christoph Erdelen, Leichlingen (DE); Wolfram Andersch, Bergisch Gladbach (DE); Ulrike Wachendorff-Neumann, Neuwied (DE); Andreas Turberg, Haan (DE); Norbert Mencke, Leverkusen (DE)

(73) Assignee: Bayer Aktiengesellschaft, Leverksusen (DE)

( * ) Notice: Subject to any disclaimer, the term of this patent is extended or adjusted under 35 U.S.C. 154(b) by 0 days.

(21) Appl. No.: 10/261,855

(22) Filed: Oct. 1, 2002

(65) Prior Publication Data

US 2003/0119828 A1 Jun. 26, 2003

Related U.S. Application Data

(62) Division of application No. 09/582,679, filed on Jun. 28, 2000, now Pat. No. 6,503,912.

(30) Foreign Application Priority Data

Jan. 8, 1998 (DE) .......................... 198 00 400

(51) Int. Cl.⁷ ..................... A61K 31/50; A61K 31/40; C07D 239/02; C07D 233/04; C07D 233/00
(52) U.S. Cl. ..................... 514/247; 514/256; 514/269; 514/408; 514/420; 514/428; 544/224; 544/297; 544/322; 544/330; 544/335; 548/300.1; 548/311.1; 548/326.5; 548/347.1
(58) Field of Search ................... 514/247, 256, 514/269, 408, 426, 428; 544/224, 297, 322, 330, 335; 548/300.1, 311.1, 326.5, 347.1

(56) References Cited

U.S. PATENT DOCUMENTS

| | | | |
|---|---|---|---|
| 4,803,277 A | 2/1989 | Shiokawa et al. | 514/332 |
| 4,849,432 A | 7/1989 | Shiokawa et al. | 514/341 |
| 4,914,113 A | * 4/1990 | Shiokawa et al. | 514/333 |
| 4,988,712 A | 1/1991 | Shiokawa et al. | 514/340 |

FOREIGN PATENT DOCUMENTS

WO 94/29268 12/1994

* cited by examiner

*Primary Examiner*—Mukund J. Shah
*Assistant Examiner*—Sudhaker B. Patel
(74) *Attorney, Agent, or Firm*—Richard E. L. Henderson; John E. Mrozinski, Jr.

(57) ABSTRACT

The present application provides guanidine derivatives of the formula (I)

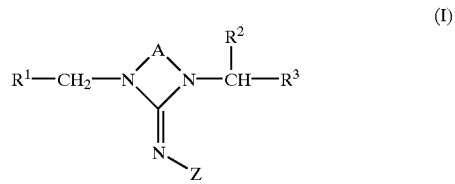

wherein $R^1$, $R^2$, $R^3$, A and Z are as defined herein.

7 Claims, No Drawings

SUBSTITUTED GUANIDINE DERIVATIVES

This application is a divisional of U.S. Ser. No. 09/582,679 filed on Jun. 28, 2000 now U.S. Pat. No. 6,503,912.

FIELD OF THE INVENTION

The present application relates to novel guanidine derivatives, to a process for their preparation and to their use for controlling animal pests.

BACKGROUND OF THE INVENTION

It is already known that certain heterocyclic compounds have insecticidal properties (cf., for example, EP-A 0 192 060, EP-A 0 277 317, Literature references according to CA 125, 188 277; 121, 255 796; 121, 157 642).

However, in particular at low application rates and concentrations, the activity and/or activity spectrum of these compounds is not entirely satisfactory in all areas of use.

DETAILED DESCRIPTION OF THE INVENTION

This invention, accordingly, provides novel guanidine derivatives of the formula (I)

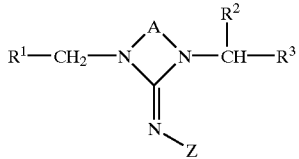

(I)

in which
- $R^1$ represents a five- or six-membered heterocyclic grouping which contains 1, 2, 3 or 4 nitrogen atoms and/or one or two oxygen or sulphur atoms as heteroatom ring members—where the number of heteroatoms is 1, 2, 3 or 4—and which is optionally substituted by halogen, cyano, nitro, alkyl, halogeno-alkyl, alkenyl, halogenoalkenyl, alkinyl, alkoxy, halogenoalkoxy, alkenyloxy, halogenoalkenyloxy, alkinyloxy, alkylthio, halogenoalkylthio, alkenylthio, halogenoalkenylthio, alkinylthio, alkylsinphinyl, halogenoalkylsinphinyl, alkylsulphonyl, halogenoalkylsulphonyl, amino, alkylamino, dialkylamino, aryl, arylthio, arylamino, aralkyl, formylamino, alkylcarbonylamino, formyl, carbamoyl, alkylcarbonyl and/or alkoxycarbonyl;
- $R^2$ represents hydrogen or alkyl,
- $R^3$ represents the groupings $-OR^4$, $-OCOR^5$, $-OCOOR^6$, $-OCONR^7R^8$ and $-OSO_2R^9$, where
  - $R^4$, $R^5$ and $R^6$ independently of one another represent alkyl, alkoxyalkyl, halogenoalkyl, alkenyl, alkinyl, alkylaminoalkyl, dialkylaminoalkyl, optionally substituted cycloalkyl and in each case optionally substituted phenyl or benzyl,
  - $R^7$ and $R^8$ independently of one another represent hydrogen, alkyl, alkenyl and in each case optionally substituted phenyl or benzyl and
  - $R^9$ represents alkyl or optionally substituted phenyl,
- A represents the groupings $-CH_2CH_2-$, $(CH_2)_3$ and $-CH=CH-$ and
- Z represents cyano or nitro, with the proviso that, if Z represents $NO_2$ and A represents $-CH_2CH_2-$, the radical $R^2$ represents hydrogen; and the compound of the formula (I) in which

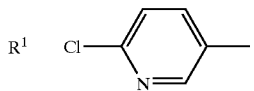

- $R^2$ H,
- $R^3$ $OCH_3$,
- A $-CH_2CH_2-$ and
- Z $NO_2$ is excluded.

Furthermore, it has been found that the compounds of the formula (I) are obtained when compounds of the formula (II)

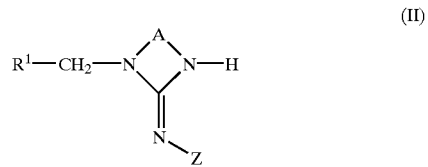

(II)

in which
- $R^1$, A and Z are as defined above are reacted with halogen compounds of the formula (III)

(III)

in which
- $R^2$ and $R^3$ are as defined above and
- X represents halogen (in particular chlorine or bromine), in the presence of a base and if appropriate in the presence of a diluent.

Finally, it has been found that the novel compounds of the formula (I) have highly pronounced biological properties and are suitable especially for controlling animal pests, in particular insects, arachnids and nematodes, encountered in agriculture, in forests, in the protection of stored products and materials and in the hygiene sector.

The formula (I) provides a general definition of the compounds according to the invention.

Preferred substituents or ranges of the radicals listed in the formulae mentioned above and below are illustrated below.

- $R^1$ preferably represents a five- to six-membered heterocyclic grouping from the group consisting of pyrazolyl, 1,2,4-triazolyl, oxazolyl, isoxazolyl, thiazolyl, isothiazolyl, 1,2,5-thiadiazolyl, pyridyl, pyrazinyl and pyrimidinyl, which is optionally substituted by fluorine, chlorine, bromine, cyano, nitro, $C_1$–$C_2$-alkyl (which is optionally substituted by fluorine and/or chlorine), $C_1$–$C_2$-alkoxy (which is optionally substituted by fluorine and/or chlorine), $C_1$–$C_2$-alkylthio (which is optionally substituted by fluorine and/or chlorine), or $C_1$–$C_2$-alkylsulphonyl (which is optionally substituted by fluorine and/or chlorine),
- $R^2$ preferably represents hydrogen or $C_1$–$C_6$-alkyl, $R^3$ preferably represents the groupings —$OR^4$, —$OCOR^5$, —$OCOOR^6$, —$OCONR^7R^8$ and —$OSO_2R^9$, where $R^4$, $R^5$ and $R^6$ independently of one another preferably represent $C_1$–$C_{12}$-alkyl, $C_1$–$C_4$-alkoxy-$C_1$–$C_4$-alkyl, $C_1$–$C_4$-halogenoalkyl having 1 to 5 identical or different halogen atoms, such as fluorine, chlorine and bromine atoms; $C_2$–$C_4$-alkenyl, $C_2$–$C_4$-alkinyl, $C_1$–$C_4$-alkylamino-$C_1$–$C_4$-alkyl, di($C_1$–$C_4$)-alkylamino-$C_1$–$C_4$-alkyl, represent $C_3$–$C_6$-cycloalkyl which is optionally mono- to trisubstituted by identical or different substituents, preferred substituents which may be mentioned being: halogen, $C_1$–$C_4$-alkyl and $C_1$–$C_4$-halogenoalkyl having 1 to 5 identical or different halogen atoms, such as F, Cl and Br atoms, or represent phenyl or benzyl, each of which is optionally mono- to trisubstituted by identical or different substituents, preferred phenyl substituents being in each case: halogen, $C_1$–$C_4$-alkyl, $C_1$–$C_4$-alkoxy and $C_1$–$C_4$-halogenoalkyl and $C_1$–$C_4$-halogenoalkoxy having in each case 1 to 5 identical or different halogen atoms, such as fluorine, chlorine and bromine atoms and nitro.

$R^7$ and $R^8$ independently of one another preferably represent hydrogen, $C_1$–$C_6$-alkyl, $C_2$–$C_4$-alkenyl or represent phenyl or benzyl, each of which is mono- to trisubstituted by identical or different substituents, preferred phenyl substituents being in each case: halogen, $C_1$–$C_4$-alkyl, $C_1$–$C_4$-alkoxy and $C_1$–$C_4$-halogenoalkyl and $C_1$–$C_4$-halogenoalkoxy having in each case 1 to 5 identical or different halogen atoms, such as fluorine, chlorine and bromine atoms; and $R^9$ preferably represents $C_1$–$C_4$-alkyl or represents phenyl which is mono- to trisubstituted by identical or different substituents, possible substituents being: halogen, $C_1$–$C_4$-alkyl, $C_1$–$C_4$-alkoxy and $C_1$–$C_4$-halogenoalkyl and $C_1$–$C_4$-halogenoalkoxy having in each case 1 to 5 identical or different halogen atoms, such as fluorine, chlorine and bromine atoms, A preferably represents the groupings —$CH_2CH_2$—, —$(CH_2)_3$— and —$CH=CH$—.

Z preferably represents cyano or nitro, with the proviso that, if Z represents $NO_2$ and A represents —$CH_2CH_2$—, the radical $R^2$ represents hydrogen; and the compound of the formula (I) in which

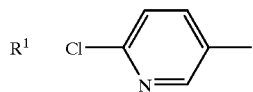

$R^2$ H,
$R^3$ $OCH_3$,
A —$CH_2CH_2$— and
Z $NO_2$
is excluded.

$R^1$ particularly preferably represents 6-chloro-3-pyridyl (6-chloro-pyridin-3-yl) or represents 2-chloro-5-thiazolyl (2-chloro-thiazol-5-yl), $R^2$ particularly preferably represents hydrogen or $C_1$–$C_5$-alkyl, $R^3$ particularly preferably represents the groupings —$OR^4$, —$OCOR^5$, —$OCOOR^6$, —$OCONR^7R^8$ and —$OSO_2R^9$, where $R^4$, $R^5$ and $R^6$ independently of one another particularly preferably represent $C_1$–$C_8$-alkyl, $C_1$–$C_2$-alkoxy-$C_1$–$C_2$-alkyl, $C_1$–$C_2$-halogenoalkyl having 1 to 2 identical or different halogen atoms, such as fluorine, chlorine and bromine atoms; allyl, propargyl, $C_1$–$C_2$-alkylamino-$C_1$–$C_2$-alkyl, di($C_1$–$C_2$)-alkylamino-$C_1$–$C_2$-alkyl, cyclopropyl, cyclopentyl, cyclohexyl or represent phenyl or benzyl, each of which is optionally mono- to disubstituted by identical or different substituents, possible phenyl substituents being in each case: fluorine, chlorine, bromine, methyl, methoxy, trifluoromethyl, trifluoromethoxy and nitro.

$R^7$ and $R^8$ independently of one another particularly preferably represent hydrogen, $C_1$–$C_4$-alkyl, vinyl, allyl or represent phenyl or benzyl, each of which is optionally mono- to disubstituted by identical or different substituents, possible phenyl substituents being in each case: fluorine, chlorine, bromine, methyl, methoxy, trifluoromethyl and trifluoromethoxy; and $R^9$ particularly preferably represents methyl, ethyl or phenyl which is optionally mono- to disubstituted by identical or different substituents, possible substituents being: fluorine, chlorine, bromine, methyl, methoxy, trifluoromethyl and trifluoromethoxy, A particularly preferably represents the groupings —$CH_2CH_2$— and —$CH=CH$—, Z particularly preferably represents cyano or nitro, with the proviso that, if Z represents $NO_2$ and A represents —$CH_2CH_2$—, the radical $R^2$ represents hydrogen; and the compound of the formula (I) in which

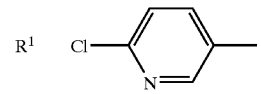

$R^2$ H,
$R^3$ $OCH_3$,
A —$CH_2CH_2$— and
Z $NO_2$
is excluded.

Preferred compounds according to the invention are substances of the formulae (I A) to (I D):

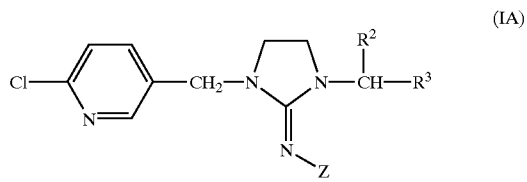
(IA)

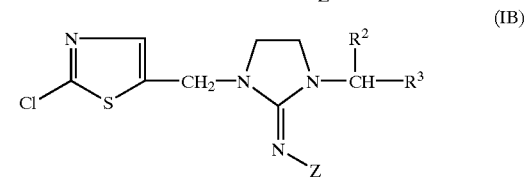
(IB)

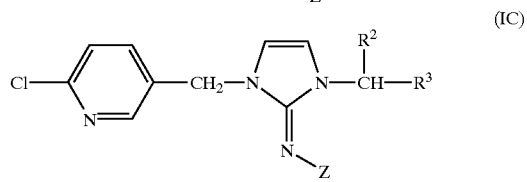
(IC)

(ID) 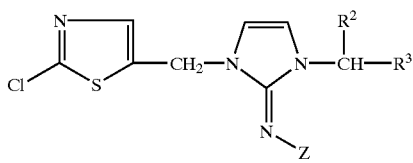

in which

R², R³ and Z have the general, preferred and particularly preferred meanings mentioned above.

Preferred compounds according to the invention are also substances of the formulae (I A-1), (I A-2), (I B-1), (I B-2), (I C-1), (I C-2), (I D-1) and (I D-2):

(IA-1) 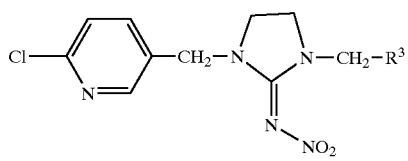

(IA-2) 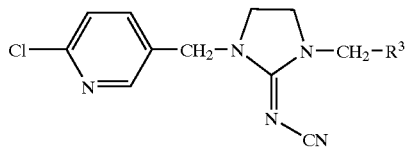

(IB-1) 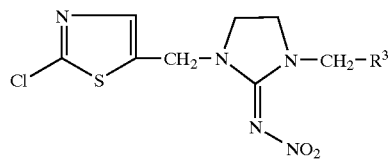

(IB-2)

(IC-1) 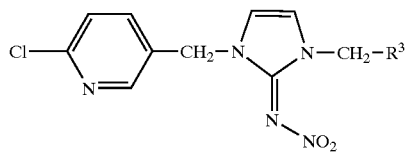

(IC-2) 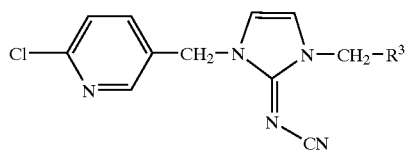

(ID-1) 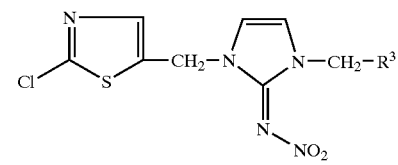

(ID-2) 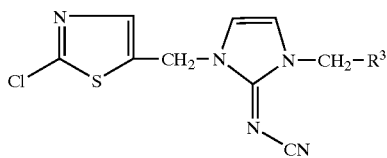

in which

R³ has the general, preferred and particularly preferred meanings mentioned above.

The abovementioned general or preferred radical definitions or illustrations apply to the end products and, correspondingly, to the starting materials and intermediates. These radical definitions can be combined with one another as desired, i.e. including combinations between the respective preferred ranges.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

In the radical definitions given above and below, hydrocarbon chains, such as alkyl—including in combination with heteroatoms such as alkoxy—are in each case straight-chain or branched as far as this is possible.

Using, for example, 1-(6-chloro-pyridin-3-yl-methyl)-2-nitroimino-imidazoline and i-propoxymethyl chloride as starting materials, the course of the process according to the invention can be represented by the following reaction scheme:

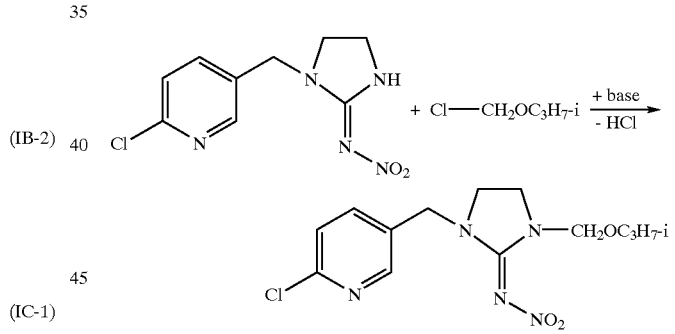

The compounds of the formula (II) required as starting materials for carrying out the process according to the invention are known (cf., for example, EP-A 0 192 060, EP-A 0 235 725, EP-A 0 259 738 and EP-A 0 315 826), and/or they can be obtained in the manner described therein.

The halogen compounds of the formula (III) further to be used as starting materials in the process according to the invention are generally known compounds of organic chemistry and/or are obtainable by generally known methods.

The process according to the invention for preparing the novel compounds of the formula (I) is preferably carried out using diluents. Suitable diluents are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric triamide.

Bases which can be used in the process according to the invention are all customary proton acceptors. Preference is given to using alkali metal or alkaline earth metal hydroxides, alkali metal or alkaline earth metal hydrides, alkali metal or alkaline earth metal carbonates or bicarbonates or nitrogen bases. Examples which may be mentioned are sodium hydroxide, calcium hydroxide, sodium hydride, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

The reaction temperatures in the process according to the invention can be varied within a relatively wide range. In general, the process is carried out at temperatures between −40° C. and +200° C., preferably between −10° C. and 100° C.

When carrying out the process according to the invention for preparing the compounds of the formula (I), generally 1 to 3 mol, preferably 1 to 2 mol, of the halogen compound of the formula (III) are employed per mole of compounds of the formula (II).

Work-up and isolation of the end products are carried out in the conventional manner.

The active compounds are suitable for controlling animal pests, in particular insects, arachnids and nematodes, encountered in agriculture, in forests, in the protection of stored products and of materials, and in the hygiene sector, and have good plant tolerance and low toxicity to warm-blooded animals. They may preferably be used as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae*, Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana*, Heliothis spp., *Spodoptera exigua, Mamestra brassicae, Panolis flammea, Spodoptera litura,* Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dernestes spp., Trogoderma spp., Anthrenus spp., Attagenus spp., Lyctus spp., *Meligethes aeneus*, Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include Pratylenchus spp., *Radopholus similis, Ditylenchus dipsaci, Tylenchulus semipenetrans*, Heterodera spp., Globodera spp., Meloidogyne spp., Aphelenchoides spp., Longidorus spp., Xiphinema spp., Trichodorus spp.

The compounds of the formula (I) according to the invention in particular have high insecticidal activity.

They can be used particularly successfully for controlling plant-damaging leaf and soil insects, such as, for example, against mosquito larvae (*Aedes aegypti*), against the black bean aphid (*Aphis fabae*), against the eggs of the onion fly (*Hylemyia antiqua*), against the peach aphid (*Myzus persicae*), against the green rice leaf-hopper (*Neophotettix cincticeps*), against the larvae of the mustard beetle (*Phaedon cochleariae*), and against the larvae of the army worm (*Spodoptera frugiperda*).

Additionally, the compounds according to the invention also have root-systemic action.

The active compounds can be converted to the customary formulations, such as solutions, emulsions, wettable powders, suspensions, powders, dusting agents, pastes, soluble powders, granules, suspension emulsion concentrates, natural and synthetic materials impregnated with active compound and very fine encapsulations in polymeric substances.

These formulations are produced in a known manner, for example by mixing the active compounds with extenders, that is liquid solvents and/or solid carriers, if appropriate with the use of surfactants, that is emulsifiers and/or dispersants and/or foam-formers.

If the extender used is water, it is also possible to use, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are:

for example ammonium salts and ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example ligninsulphite waste liquors and methylcellulose.

Tackifiers such as carboxymethylcellulose and natural and synthetic polymers in the form of powders, granules or latices such as gum arabic, polyvinyl alcohol and polyvinyl acetate, and natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention can be present in its commercially available formulations and in the use forms prepared from these formulations as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous mixing components are the following:

Fungicides:
aldimorph, ampropylfos, ampropylfos potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
uniconazole,
validamycin A, vinclozolin, viniconazole,
zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-b-propyl-1H-1,2,4-triazole-1-ethanol,
α-(2,4-dichlorophenyl)-β-methoxy-a-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole1-ethanol,
(5RS,6RS)-6-hydroxy-2,2,7,7-tetramethyl-5-(1H-1,2,4-triazol-1-yl)-3-octanone,
(E)-a-(methoxyimino)-N-methyl-2-phenoxy-phenylacetamide,
isopropyl {2-methyl-1-[[[1-(4-methylphenyl)-ethyl]-amino]-carbonyl]-propyl}-carbamate,
1-(2,4-dichloropbenyl)-2-(1H-1,2,4-triazol-1-yl)-ethanone O-(phenylmethyl)-oxime,
1-(2-methyl-1-naphthalenyl)-1H-pyrrol-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoro-methyl-1,3-thiazole-5-carboxanilide
2,2-dichloro-N-[1-(4-chlorophenyl)-ethyl]-1-ethyl-3-methyl-cyclopropane-carboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrol-2,5-dione,
3,5-dichloro-N-[cyano-[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethylmorpholinehydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methaneimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramido-thioate,
S-methyl 1,2,3-benzothiadiazole-7-carbothioate,
spiro[2H]-1-benzopyran-2,1'(3'H)-isobenzofuran]-3'-one, Bactericides:
  bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
  abamectin, AC 303 630, acephate, acrinathrin, alanycarb, aldicarb, alphamethrin, amitraz, avermectin, AZ 60541, azadirachtin, azinphos A, azinphos M, azocyclotin, AKD 1022,
  Bacillus thuringiensis, bendiocarb, benfuracarb, bensultap, betacyfluthrin, bifenthrin, BPMC, brofenprox, bromophos A, bufencarb, buprofezin, butocarboxim, butylpyridaben,
  cadusafos, carbaryl, carbofuran, carbophenothion, carbosulfan, cartap, CGA 157 419, CGA 184 699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
  deltamethrin, demeton M, demeton S, demeton S-methyl, diaeloden, diafenthiuron, diazinon, dichlofenthion, dichlorvos, dicliphos, dicrotophos, diethion, diflubenzuron, dimethoate, dimethylvinphos, dioxathion, disulfoton,
  edifenphos, emamectin, esfenvalerate, ethiofencarb, ethion, ethofenprox, ethoprophos, etrimphos,
  fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb,
  HCH, heptenophos, hexaflumuron, hexythiazox,
  imidacloprid, iprobenfos, isazophos, isofenphos, isoprocarb, isoxathion, ivermectin,
  lambda-cyhalothrin, lufenuron,
  malathion, mecarbam, mevinphos, mesulfenphos, metaldehyde, methacrifos, methamidophos, methidathion, methiocarb, methomyl, metolcarb, milbemectin, monocrotophos, moxidectin,
  naled, NC 184, NI 25, nitenpyram,
  omethoate, oxamyl, oxydemethon M, oxydeprofos,
  parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen,
  quinalphos,
  RH 5992
  salithion, sebufos, silafluofen, sulfotep, sulprofos,
  tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, TI 435,
  vamidothion, XMC, xylylcarb, YI 5301/5302, zetamethrin.

It is also possible to admix other known active compounds, such as herbicides, or fertilizers and growth-regulating substances.

When used as insecticides, the active compounds according to the invention can furthermore be present in their commercial formulations and in the use forms prepared from these formulations, as a mixture with synergists. Synergists are compounds which increase the activity of the active compounds, without it being necessary for the added synergist to be active itself.

The active compound content of the use forms prepared from the commercial formulations can vary within wide ranges. The active compound concentration of the use forms can be from 0.0000001 to 95% by weight of active compound, and is preferably between 0.0001 and 1% by weight.

The application is carried out in a manner which is adapted to the use forms.

When used against hygiene pests and pests of stored products, the active compound is distinguished by excellent residual activity on wood and clay, and by good stability to alkali on limed substrates.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, Haematopinus spp., Linognathus spp., Pediculus spp., Phtirus spp. and Solenopotes spp.

From the order of the Mallophagida and the suborders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example *Blatta orientalis, Periplaneta americana, Blattela germanica* and Supella spp.

From the subclass of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The compounds according to the invention have, for example, good development-inhibitory action against fly larvae of *Lucilia cuprina*.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice.

The active compounds according to the invention are used in the veterinary sector in a known manner by enteral administration in the form of, for example, tablets, capsules, potions, drenches, granules, pastes, boluses, the feed-through process by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10,000-fold dilution, or they can be used as a chemical bath.

It has furthermore been found that the compounds of the formula (I) according to the invention have a strong insecticidal action against insects which destroy industrial materials.

The following insects may be mentioned as examples and as preferred—but without a limitation:

Beetles, such as
  *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec. Tryptodendron spec. *Apate monachus, Bostrychus capucins, Heterobostrychus brunneus,* Sinoxylon spec. *Dinoderus minutus.*

Hymenopterons, such as
  *Sirex juvencus, Urocerus gigas, Urocerus gigas taignus, Urocerus augur*

Termites, such as
  *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccarina*.

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising these are to be understood as meaning, for example: building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flash point above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., turpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flash point above 30° C., preferably above 45° C., can be replaced in part by organic chemical solvents of high or medium volatility, providing that the solvent mixture likewise has an evaporation number above 35 and a flash point above 30° C., preferably above 45° C., and that the insecticide/fungicide mixture is soluble or emulsifiable in this solvent mixture.

According to a preferred embodiment, some of the organic chemical solvent or solvent mixture or an aliphatic polar organic chemical solvent or solvent mixture is replaced. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing components are, preferably, the insecticides and fungicides mentioned in Wo 94/29 268. The compounds mentioned in this document are an explicit constituent of the present application.

Especially preferred mixing components which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The preparation and the use of the active compounds according to the invention are illustrated by the examples below.

PREPARATION EXAMPLES

Example 1

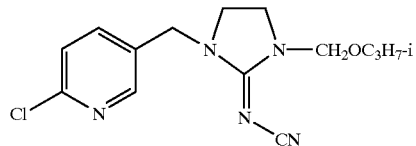

At 5° C., 1.5 g (0.0063 mol) 1-(6-chloro-pyridin-3-yl-methyl)-2-cyanoimino-imidazolidine in 25 ml of absolute dimethylformamide are admixed with stirring with 0.25 g (0.0063 mol) of sodium hydride, a little at a time. After 1 hour of stirring at room temperature, 0.7 ml (0.0063 mol) of i-propoxymethyl chloride are added at 0° C., and the mixture is stirred overnight. The reaction mixture is concentrated by distilling off the solvent and the residue is taken up in petroleum ether and filtered. The filtrate is purified by silica gel column chromatography (methylene chloride/methanol: 15/0.5).

This gives 0.57 g (29% of theory) of 1-(6-chloro-pyridin-3-yl-methyl)-2-cyanoimino-3-i-propoxymethyl-imidazolidine of melting point 85–87° C.

Example 2

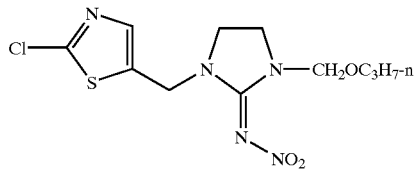

With stirring, 1.5 g (5.7 mmol) of 1-(2-chloro-thiazol-5-yl-methyl)-2-nitroimino-imidazolidine in 5 ml of absolute dimethylformamide are admixed a little at a time with 0.26 g (6.5 mmol) of sodium hydride. The mixture is stirred at room temperature for a short while, 0.70 g (6.5 mmol) of n-propoxymethyl chloride is added with cooling and the mixture is stirred overnight. The reaction mixture is concentrated under reduced pressure and the residue is admixed with water and extracted with methylene chloride. The organic phase is dried over sodium sulphate and concentrated and the residue is stirred with diisopropyl ether and reconcentrated.

This gives 1.54 g (76% of theory) of 1-(2-chloro-thiazol-5-yl-methyl)-2-nitroimino-3-n-propoxymethyl-imidazolidine of calculated index $n_D^{20}$=1.5781.

Example 3

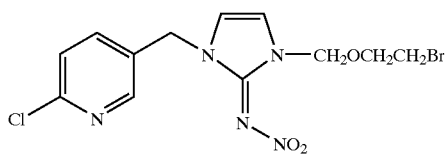

At room temperature, 2.54 g (0.01 mol) of 1-(6-chloro-pyridin-3-yl-methyl)-2-nitroimino-imidazoline in 10 ml of absolute dimethylformamide are admixed, a little at a time, with 0.44 g (0.011 mol) of sodium hydride. The mixture is stirred for a short while, 2.17 g (0.0125 mol) of bromoethoxymethyl chloride are added with cooling and the mixture is stirred at room temperature overnight. The reaction mixture is concentrated under reduced pressure and the residue is admixed with water and extracted with methylene chloride. The organic phase is dried over sodium sulphate and concentrated and the residue is stirred in diisopropyl ether and filtered. The filtrate is purified by silica gel column chromatography (methylene chloride/methanol: 10/1).

This gives 2.3 g (53% of theory) of 1-(6-chloro-pyridin-3-yl-methyl)-2-nitroimino-3-bromoethoxymethyl-imidazoline of melting point 90–92° C.

The compounds listed in Table 1 below are obtained analogously to the Preparation Examples 1 to 3 and in accordance with the general statements about the preparation of the compounds of the formula (I):

| Ex. No. | $R^1$ | A | $R^2$ | $R^3$ | Z | Physical const. (m.p. ° C.) or logP (pH = 2.3) *) |
|---|---|---|---|---|---|---|
| 4 | 6-chloro-pyridin-3-yl | —CH$_2$CH$_2$— | H | —OC$_2$H$_5$ | NO$_2$ | 66–69 |
| 5 | 6-chloro-pyridin-3-yl | —CH$_2$CH$_2$— | H | —OC$_8$H$_{17}$-n | NO$_2$ | 3.55 |
| 6 | 6-chloro-pyridin-3-yl | —CH=CH— | H | —OC$_2$H$_5$ | NO$_2$ | 1.09 |
| 7 | 6-chloro-pyridin-3-yl | —CH=CH— | H | —OC$_8$H$_{17}$-n | NO$_2$ | 101–03 |
| 8 | 6-chloro-pyridin-3-yl | —CH$_2$CH$_2$— | H | —OCO—C$_6$H$_4$—CH$_3$ | NO$_2$ | 98–100 |
| 9 | 6-chloro-pyridin-3-yl | —CH=CH— | H | —OCH$_3$ | NO$_2$ | 0.78 |
| 10 | 6-chloro-pyridin-3-yl | —CH$_2$CH$_2$— | H | —OC$_3$H$_7$-n | NO$_2$ | 1.64 |
| 11 | 6-chloro-pyridin-3-yl | —CH=CH— | H | —OC$_3$H$_7$-n | NO$_2$ | 64–66 |
| 12 | 6-chloro-pyridin-3-yl | —CH$_2$CH$_2$— | H | —OC$_3$H$_7$-i | NO$_2$ | 70–71 |

-continued
| Ex. No. | R¹ | A | R² | R³ | Z | Physical const. (m.p. °C.) or logP (pH = 2.3) *) |
|---|---|---|---|---|---|---|
| 13 | 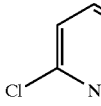 | —CH₂CH₂— | H | —OCH₂C₃H₇-i | NO₂ | 2.00 |
| 14 | 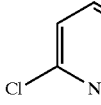 | —CH=CH— | H | —OC₃H₇-i | NO₂ | 85–87 |
| 15 | 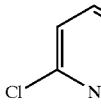 | —CH=CH— | H | —OCH₂C₃H₇-i | NO₂ | 97–99 |
| 16 | 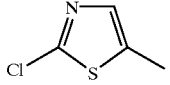 | —CH₂CH₂— | H | —OCH₃ | NO₂ | 1.14 |
| 17 | 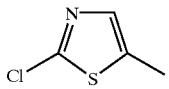 | —CH₂CH₂— | H | —OC₂H₅ | NO₂ | 1.40 |
| 18 | 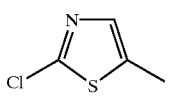 | —CH₂CH₂— | H | —OC₃H₇-i | NO₂ | 1.65 |
| 19 | 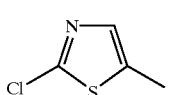 | —CH₂CH₂— | H | —OCH₂C₃H₇-i | NO₂ | 2.12 |
| 20 | 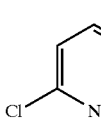 | —CH₂CH₂— | H | —OCH₂C(CH₃)₃ | NO₂ | 98–100 |
| 21 | 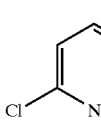 | —CH₂CH₂— | H | —OC(CH₃)C₂H₅ | NO₂ | 1.86 |
| 22 | 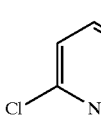 | —CH₂CH₂— | H | —OC₅H₁₁-n | NO₂ | 2.35 |
| 23 | 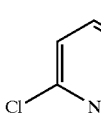 | —CH₂CH₂— | H | —OC₆H₁₃-n | NO₂ | 2.73 |
| 24 | 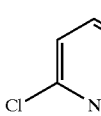 | —CH₂CH₂— | H | —OCH₂CH₂OCH₃ | NO₂ | 1.16 |
| 25 | 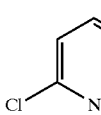 | —CH₂CH₂— | H | —OCOC(CH₃)₃ | NO₂ | 118–20 |

-continued

| Ex. No. | R¹ | A | R² | R³ | Z | Physical const. (m.p. ° C.) or logP (pH = 2.3) *) |
|---|---|---|---|---|---|---|
| 26 | 6-chloropyridin-3-yl | —CH₂CH₂— | H | —O—(4-chlorophenyl) | NO₂ | 134–35 |
| 27 | 6-chloropyridin-3-yl | —CH₂CH₂— | H | —OCH₂C₃H₇-i | CN | 77 |
| 28 | 6-chloropyridin-3-yl | —CH₂CH₂— | H | —OCH₂C(CH₃)₃ | CN | 132–33 |
| 29 | 6-chloropyridin-3-yl | —CH₂CH₂— | H | —OCH₃ | CN | 1.32 |
| 30 | 6-chloropyridin-3-yl | —CH₂CH₂— | H | —OCOC(CH₃)₃ | CN | 102–03 |
| 31 | 6-chloropyridin-3-yl | —CH₂CH₂— | H | —OCH₂CH₂OCH₃ | CN | 1.40 |
| 32 | 6-chloropyridin-3-yl | —CH₂CH₂— | H | —OC₃H₇-n | CN | 1.89 |
| 33 | 6-chloropyridin-3-yl | —CH₂CH₂— | H | —OCOCH₃ | NO₂ | 109–11 |
| 34 | 6-chloropyridin-3-yl | —CH₂CH₂— | H | —OCH₂-phenyl | NO₂ | 2.06 |
| 35 | 6-chloropyridin-3-yl | —CH₂CH₂— | H | —OCOC₂H₅ | NO₂ | 1.50 |
| 36 | 6-chloropyridin-3-yl | —CH₂CH₂— | H | —OCOC₃H₇-i | NO₂ | 82 |
| 37 | 6-chloropyridin-3-yl | —CH₂CH₂— | H | —OCOCH₃ | CN | 85–87 |
| 38 | 6-chloropyridin-3-yl | —CH₂CH₂— | H | —OCOC₂H₅ | CN | 75 |

-continued

| Ex. No. | R¹ | A | R² | R³ | Z | Physical const. (m.p. ° C.) or logP (pH = 2.3) *) |
|---|---|---|---|---|---|---|
| 39 | 6-Cl-pyridin-3-yl | —CH₂CH₂— | H | —OCOC₃H₇-i | CN | 85–86 |
| 40 | 6-Cl-pyridin-3-yl | —CH₂CH₂— | H | —OC₄H₉-n | NO₂ | 1.98 |
| 41 | 6-Cl-pyridin-3-yl | —CH=CH— | H | —OC₄H₉-n | NO₂ | 1.72 |
| 42 | 6-Cl-pyridin-3-yl | —CH₂CH₂— | H | —OCH₂-C₆H₅ | CN | 113 |
| 43 | 6-Cl-pyridin-3-yl | —CH₂CH₂— | H | —OCH₂CH₂N(C₂H₅)₂ | NO₂ | 0.70 |
| 44 | 6-Cl-pyridin-3-yl | —CH₂CH₂— | H | —OCH₂CH=CH₂ | NO₂ | 69–71 |
| 45 | 6-Cl-pyridin-3-yl | —CH₂CH₂— | H | —OCH₂C≡CH | NO₂ | 68–69 |
| 46 | 6-Cl-pyridin-3-yl | —CH₂CH₂— | H | —OCO-C₆H₅ | CN | 122–24 |
| 47 | 6-Cl-pyridin-3-yl | —CH₂CH₂— | H | —OCO-C₆H₄-4-CH₃ | NO₂ | 144 |
| 48 | 6-Cl-pyridin-3-yl | —CH₂CH₂— | H | —OCO-C₆H₄-4-Cl | NO₂ | 137 |
| 49 | 6-Cl-pyridin-3-yl | —CH₂CH₂— | H | —OCO-C₆H₄-4-CH₃ | CN | 146 |
| 50 | 6-Cl-pyridin-3-yl | —CH=CH— | H | —OCO-C₆H₄-4-CH₃ | NO₂ | 144 |

-continued

| Ex. No. | R¹ | A | R² | R³ | Z | Physical const. (m.p. ° C.) or logP (pH = 2.3) *) |
|---|---|---|---|---|---|---|
| 51 | 6-Cl-pyridin-3-yl | —CH₂CH₂— | H | —OCO—C₆H₄—F | NO₂ | 141 |
| 52 | 6-Cl-pyridin-3-yl | —CH₂CH₂— | H | —OCO—cyclohexyl | NO₂ | 110 |
| 53 | 6-Cl-pyridin-3-yl | —CH₂CH₂— | H | —O—(CH₂)₂—Br | NO₂ | 1.64 |
| 54 | 6-Cl-pyridin-3-yl | —CH₂CH₂— | CH₃ | —OC₃H₇-n | NO₂ | 93–95 |
| 55 | 6-Cl-pyridin-3-yl | —CH₂CH₂— | H | —O—(cyclohexyl-NO₂) | NO₂ | 102–05 |
| 56 | 6-Cl-pyridin-3-yl | —(CH₂)₃— | H | —OC₃H₇-i | NO₂ | 1.34 |
| 57 | 6-Cl-pyridin-3-yl | —(CH₂)₃— | H | —O—CO—C₄H₉-t | NO₂ | 143–44 |
| 58 | 6-Cl-pyridin-3-yl | —CH₂CH₂— | CH₃ | —O—CH₂—CH=CH₂ | NO₂ | 75–77 |
| 59 | 6-Cl-pyridin-3-yl | —CH₂CH₂— | H | —O—CO—cyclopropyl | NO₂ | 1.57 |

[logP = The logP values were determined in accordance with EEC directive 79/831 Annex V. A8 by HPLC (gradient method, acetonitrile/0.1% aqueous phosphoric acid]

Use Examples

Example A

Aedes Test

Solvent: 1000 parts by weight of methanol

To produce a suitable preparation of active compound, 1 part by weight of active compound is mixed with the stated amount of solvent, and the concentrate is diluted with water to the desired concentrations.

Mosquito larvae (*Aedes aegypti*) are placed into the preparation of active compound of the desired concentration.

After the desired period of time, the effect on the larvae is determined. 100% means that all animals exhibit serious symptoms or have been killed; 0% means that no animals have been killed.

In this test, at an exemplary active compound concentration of 0.0016%, the compounds of Preparation Examples 4, 5 and 7 effected a kill of 100%, in each case after 4 hours.

Example B

Aphis Test (Systemic Action)

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent, and the stated amount of emulsifier, and the concentrate is diluted with water to the desired concentration.

Bean plants (*Vicia faba*) which are heavily infested by the black bean aphid (*Aphis fabae*) are watered with in each case 20 ml of the preparation of active compound of the desired concentration so that the preparation of active compound penetrates into the soil without wetting the shoot. The active compound is taken up by the roots and passed on to the shoot.

After the desired period of time, the kill in % is determined. 100% means that all aphids have been killed; 0% means that none of the aphids has been killed.

In this test, at an exemplary active compound concentration of 0.01%, the compounds of:

Preparation Examples 4 and 9 effected a kill of 100% the
    Preparation Example 5 effected a kill of 95%
in each case after 4 days.

Example C
Hylemyia Test

| Solvent: | 100 parts by weight of acetone |
| --- | --- |
|  | 1900 parts by weight of methanol |

To produce a suitable preparation of active compound, 1 part by weight of active compound is mixed with the stated amount of solvent, and the concentrate is diluted with methanol to the desired concentration.

A stated amount of the preparation of active compound of the desired concentration is pipetted onto a standardized quantity of artificial feed. After the methanol has evaporated, about 20 eggs of the onion fly (*Hylemyia antiqua*) are placed on the feed.

After the desired period of time, the kill of the eggs or larvae in % is determined. 100% means that all animals have been killed; 0% means that none of the animals has been killed.

In this test, at an exemplary active compound concentration of 0.05%, the compound of Preparation Example 4 effected a kill of 100% after 7 days.

Example D
Myzus Test

| Solvent: | 7 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amount of solvent, and the stated amount of emulsifier, and the concentrate is diluted with water to the desired concentration.

Cabbage leaves (*Brassica oleracea*) which are heavily infested by the peach aphid (*Myzus persicae*) are treated by being dipped into the preparation of active compound of the desired concentration.

After the desired period of time, the kill in % is determined. 100% means that all aphids have been killed; 0% means that none of the aphids has been killed.

In this test, at an exemplary active compound concentration of 0.1%, the compounds of Preparation Examples 10, 11, 12, 13, 14, 15, 16, 17, 18, 20, 25 and 36 effected a kill of 100%, in each case after 6 days.

Example E
Nephotettix Test

| Solvent: | 7 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amount of solvent, and the stated amount of emulsifier, and the concentrate is diluted with water to the desired concentration.

Rice seedlings (*Oryza sativa*) are treated by being dipped into the preparation of active compound of the desired concentration and are populated with larvae of the green rice leaf-hopper (*Nephotettix cincticeps*) while the seedlings are still moist.

After the desired period of time, the kill in % is determined. 100% means that all leaf-hoppers have been killed; 0% means that none of the leaf-hoppers has been killed.

In this test, at an exemplary active compound concentration of 0.1%, the compounds of Preparation Examples 4, 10, 12, 13, 14, 15, 18, 19, 21, 24, 25, 26, 33 and 36 effected a kill of 100%, in each case after 6 days.

Example F
Phaedon Larvae Test

| Solvent: | 7 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with mustard beetle larvae (*Phaedon cochleariae*) whilst the leaves are still moist.

After the desired period of time, the kill in % is determined. 100% means that all beetle larvae have been killed; 0% means that none of the beetle larvae has been killed.

In this test, at an exemplary active compound concentration of 0.1%, the compounds of Preparation Examples 4, 10, 12, 17, 18, 19, 21, 25, 33, 34, 35 and 36 effected a kill of 100, in each case after 7 days.

Example G
Spodoptera frugiperda test

| Solvent: | 7 parts by weight of dimethylformamide |
| --- | --- |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

Cabbage leaves (*Brassica oleracea*) are treated by being dipped into the preparation of active compound of the desired concentration and are populated with larvae of the army worm (*Spodoptera frugiperda*) whilst the leaves are still moist.

After the desired period of time, the kill in % is determined. 100% means that all larvae have been killed; 0% means that none of the larvae has been killed.

In this test, at an exemplary active compound concentration of 0.1%, the compounds of Preparation Examples 2, 10, 12, 13, 17, 18, 20, 25, 33, 35 and 36 effected a kill of 100, in each case after 7 days.

Example H
Spodoptera frugiperda test/artificial feed

| Solvent: | 100 parts by weight of acetone |
| | 1900 parts by weight of methanol |

To produce a suitable preparation of active compound, 1 part by weight of active compound is mixed with the stated amount of solvent, and the concentrate is diluted with methanol to the desired concentration.

A stated amount of the preparation of active compound of the desired concentration is pipetted onto a standardized quantity of artificial feed. After the methanol has evaporated, in each case one larva ($L_2$–$L_3$) of the army worm (Spodoptera frugiperda) is placed onto the feed, in 3 repetitions.

After the desired period of time, the kill in % is determined. 100% means that all animals have been killed; 0% means that none of the animals has been killed.

In this test, at an exemplary active compound concentration of 0.05%, the compound of Preparation Example 4 effected a kill of 100% after 7 days.

Example I
Critical Concentration Test/root-systemic Action

| Test insect: | Aphis fabae |
| Solvent: | 4 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is mixed intimately with soil. The concentration of the active compound in the preparation is virtually immaterial, only the amount by weight of active compound per volume unit of soil, which is stated in ppm (=mg/l), matters. The treated soil is filled into pots which are planted with pregerminated broad beans. Thus, the active compound can be taken up from the soil by the plant roots and transported into the leaves.

To demonstrate the root-systemic effect, the leaves are populated with the abovementioned test animals after 7 days. After a further 6 days, evaluation is carried out by counting or estimating the dead animals. The root-systemic action of the active compound is deduced from the number of animals killed. It is 100% when all test animals have been killed and 0% when the number of live test insects is identical to that of the untreated control.

In this test, at an exemplary active compound concentration of 20 ppm, the compounds of Preparation Examples 4 and 5 effected a kill of 100%.

Example J
Blowfly Larvae Test/development-inhibitory action

| Test animals: | Lucilia cuprina larvae |
| Solvent: | Dimethyl sulfoxide |

20 mg of active compound are dissolved in 1 ml of dimethyl sulfoxide, more dilute concentrations are prepared by dilution with Dest.$H_2O$.

About 20 Lucilia cuprina larvae are introduced into a test tube which contains about 1 $cm^3$ of horse meat and 0.5 ml of the preparation of active compound to be tested. After 24 hours and 48 hours, the effectiveness of the preparation of active compound is determined. The test tubes are transferred into beakers whose bottom is covered with sand. After a further 2 days, the test tubes are removed and the pupae are counted.

The effect of the preparation of active compound is assessed by the number of flies which have hatched after 1.5 times the development period of an untreated control. 100% means that no flies have hatched; 0% means that all flies have hatched normally.

In this test, at an exemplary active compound concentration of 100 ppm, the compounds of Preparation Examples 9, 10, 11, 12 and 13 exhibited a development-inhibitory effect of 100%.

The foregoing embodiments of the present invention are offered for the purpose of illustration and not limitation. It will be apparent to those skilled in the art that the embodiments described herein may be modified or revised in various ways without departing from the spirit and scope of the invention. The scope of the invention is to be measured by the appended claims.

What is claimed is:

1. A compound of the formula (I)

$$R^1-CH_2-N\underset{\underset{Z}{\parallel}}{\overset{A}{\diagup\hspace{-0.5em}\diagdown}}N-CH-R^3 \quad\quad R^2$$ (I)

wherein
R$^1$ represents a five- or six-membered heterocyclic grouping containing 1, 2, 3 or 4 nitrogen atoms and/or one or two oxygen or sulphur atoms as heteroatom ring members wherein the number of heteroatoms is 1, 2, 3 or 4 and which is optionally substituted by halogen, cyano, nitro, alkyl, halogenoalkyl, alkenyl, halogenoalkenyl, alkynyl, alkoxy, halogenoalkoxy, alkenyloxy, halogenoalkenyloxy, alkynyloxy, alkylthio, halogenoalkylthio, alkenylthio, halogenoalkenylthio, alkynylthio, alkylsulphinyl, halogeno-alkylsulphinyl, alkylsulphonyl, halogenoalkylsulphonyl, amino, alkylamino, dialkylamino, aryl, arylthio, arylamino, aralkyl, formylamino, alkylcarbonylamino, formyl, carbamoyl, alkylcarbonyl and/or alkoxycarbonyl;
R$^2$ represents hydrogen or alkyl,
R$^3$ represents one of the groupings —OR$^4$, —OCOR$^5$, —OCOOR$^6$, —OCONR$^7$R$^8$ and —OSO$_2$R$^9$, wherein R$^4$, R$^5$ and R$^6$ independently represent alkyl, alkoxyalkyl, halogenoalkyl, alkenyl, alkynyl, alkylaminoalkyl, dialkylaminoalkyl, optionally substituted cycloalkyl and in each case optionally substituted phenyl or benzyl, $R^7$ and $R^8$ independently represent hydrogen, alkyl, alkenyl and in each case optionally substituted phenyl or benzyl and $R^9$ represents alkyl or optionally substituted phenyl, A represents one of the groupings —$(CH_2)_3$— and —CH=CH— and Z represents cyano or nitro.

2. A process for preparing a compound of the formula (I)

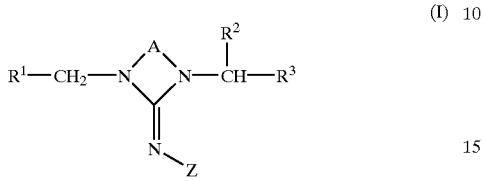

(I)

wherein $R^1$ represents a five- or six-membered heterocyclic grouping containing 1, 2, 3 or 4 nitrogen atoms and/or one or two oxygen or sulphur atoms as heteroatom ring members wherein the number of heteroatoms is 1, 2, 3 or 4 and which is optionally substituted by halogen, cyano, nitro, alkyl, halogenoalkyl, alkenyl, halogenoalkenyl, alkynyl, alkoxy, halogenoalkoxy, alkenyloxy, halogenoalkenyloxy, alkynyloxy, alkylthio, halogenoalkylthio, alkenylthio, halogenoalkenylthio, alkynylthio, alkylsulphinyl, halogeno-alkylsulphinyl, alkylsulphonyl, halogeno alkylsulphonyl, amino, alkylamino, dialkylamino, aryl, arylthio, arylamino, aralkyl, formylamino, alkylcarbonylamino, formyl, carbamoyl, alkylcarbonyl and/or alkoxycarbonyl;

$R^2$ represents hydrogen or alkyl, $R^3$ represents one of the groupings —$OR^4$, —$OCOR^5$, —$OCOOR^6$, —$OCONR^7R^8$ and —$OSO_2R^9$, wherein $R^4$, $R^5$ and $R^6$ independently represent alkyl, alkoxyalkyl, halogenoalkyl, alkenyl, alkynyl, alkylaminoalkyl, dialkylaminoalkyl, optionally substituted cycloalkyl and in each case optionally substituted phenyl or benzyl, $R^7$ and $R^8$ independently represent hydrogen, alkyl, alkenyl and in each case optionally substituted phenyl or benzyl and $R^9$ represents alkyl or optionally substituted phenyl, A represents one of the groupings $(CH_2)_3$ and —CH=CH— and Z represents cyano or nitro, comprising reacting a compound of the formula (II)

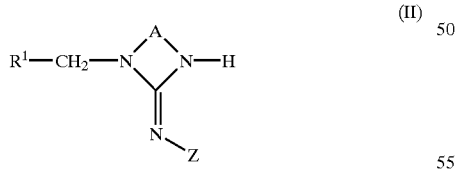

(II)

wherein $R^1$, A and Z are as defined above with a halogen compound of the formula (III)

(III)

wherein $R^2$ and $R^3$ are as defined above and

X represents halogen, in the presence of a base and optionally in the presence of a diluent.

3. The compound according to claim 1, wherein $R^1$ represents a five- to six-membered heterocyclic selected from the group consisting of pyrazolyl, 1,2,4-triazolyl, oxazolyl, isoxazolyl, thiazolyl, isoth iazolyl, 1,2,5-thiadiazolyl, pyridyl, pyrazinyl and pyrimidinyl, which is optionally substituted by fluorine, chlorine, bromine, cyano, nitro, $C_1$–$C_2$-alkyl (which is optionally substituted by fluorine and/or chlorine), $C_1$–$C_2$-alkoxy (which is optionally substituted by fluorine and/or chlorine), $C_1$–$C_2$-alkylthio (which is optionally substituted by fluorine and/or chlorine), or $C_1$–$C_2$-alkylsulphonyl (which is optionally substituted by fluorine and/or chlorine), $R^2$ represents hydrogen or $C_1$–$C_6$-alkyl, $R^3$ represents one of the groupings —$OR^4$, —$OCOR^5$, —$OCOOR^6$, —$OCONR^7R^8$ and —$OSO_2R^9$, wherein $R^4$, $R^5$ and $R^6$ independently represent $C_1$–$C_{12}$-alkyl, $C_1$–$C_4$-alkoxy-$C_1$–$C_4$-alkyl, $C_1$–$C_4$-halogenoalkyl having 1 to 5 atoms, selected from fluorine, chlorine and bromine; $C_2$–$C_4$-alkenyl, $C_2$–$C_4$-alkynyl, $C_1$–$C_4$-alkylamino-$C_1$–$C_4$-alkyl, di($C_1$–$C_4$)-alkylamino-$C_1$–$C_4$-alkyl, represent $C_3$–$C_6$-cycloalkyl which is optionally mono- to trisubstituted by substituents selected from the group consisting of halogen, $C_1$–$C_4$-alkyl and $C_1$–$C_4$-halogenoalkyl having 1 to 5 halogen atoms, or represent phenyl or benzyl, each of which is optionally mono- to trisubstituted by substituents selected from the group consisting of halogen, $C_1$–$C_4$-alkyl, $C_1$–$C_4$-alkoxy and $C_1$–$C_4$-halogenoalkyl and $C_1$–$C_4$-halogenoalkoxy having in each case 1 to 5 atoms, selected from the group consisting of fluorine, chlorine and bromine and nitro, $R^7$ and $R^8$ independently represent hydrogen, $C_1$–$C_6$-alkyl, $C_2$–$C_4$-alkenyl or represent phenyl or benzyl, each of which is mono- to trisubstituted by substituents selected from the group consisting of halogen, $C_1$–$C_4$-alkyl, $C_1$–$C_4$-alkoxy and $C_1$–$C_4$-halogenoalkyl and $C_1$–$C_4$-halogenoalkoxy having in each case 1 to 5 atoms, selected from fluorine, chlorine and bromine; and $R^9$ represents $C_1$–$C_4$-alkyl or represents phenyl which is mono- to trisubstituted by substituents selected from the group consisting of halogen, $C_1$–$C_4$-alkyl, $C_1$–$C_4$-alkoxy and $C_1$–$C_4$-halogenoalkyl and $C_1$–$C_4$-halogenoalkoxy having in each case 1 to 5 halogen atoms, selected from the group consisting of fluorine, chlorine and bromine, A represents one of the groupings —$(CH_2)_3$— and —CH=CH—, Z represents cyano or nitro.

4. The compound according to claim 1, wherein $R^1$ represents 6-chloro-3-pyridyl (6-chloro-pyridin-3-yl) or represents 2-chloro-5-thiazolyl (2-chloro-thiazol-5-yl), $R^2$ represents hydrogen or $C_1$–$C_5$-alkyl, $R^3$ represents one of the groupings —$OR^4$, —$OCOR^5$, —$OCOOR^6$, —$OCONR^7R^8$ and —$OSO_2R^9$, wherein $R^4$, $R^5$ and $R^6$ independently represent $C_1$–$C_8$-alkyl, $C_1$–$C_2$-alkoxy-$C_1$–$C_2$-alkyl, $C_1$–$C_2$-halogenoalkyl having 1 to 2 halogen atoms, selected from the group consisting of fluorine, chlorine and bromine, allyl, propargyl, $C_1$–$C_2$-alkylamino-$C_1$–$C_2$-alkyl, di($C_1$–$C_2$)-alkylamino-$C_1$–$C_2$-alkyl, cyclopropyl, cyclopentyl, cyclohexyl or represent phenyl or benzyl, each of which is optionally mono- to disubstituted by substituents selected from the group consisting of fluorine, chlorine, bromine, methyl, methoxy, trifluoromethyl, trifluoromethoxy and nitro, $R^7$ and $R^8$ independently represent hydrogen, $C_1$–$C_4$-alkyl, vinyl, allyl or represent phenyl or benzyl, each of which is optionally mono- to disubstituted phenyl substituents selected from the group consisting of fluorine, chlorine, bromine, methyl, methoxy, trifluoromethyl and trifluoromethoxy; and $R^9$ represents methyl, ethyl or phenyl which is optionally mono- to disubstituted by substituents selected from the group consisting of fluorine, chlorine, bromine, methyl, methoxy, trifluoromethyl and trifluoromethoxy, A represents —CH=CH—, Z represents cyano or nitro.

5. A composition for controlling animal pests comprising at least one compound according to claim 1.

6. In a method of controlling animal pests, the improvement comprising applying at least one compound according to claim 1.

7. A method of making a composition for controlling animal comprising mixing at least one compound according to claim 1 with one of a diluent and a surfactant.

* * * * *